(12) United States Patent  
Perez

(10) Patent No.: US 8,585,621 B1
(45) Date of Patent: Nov. 19, 2013

(54) SKIN EXFOLIATION APPARATUS

(75) Inventor: Eugenio Perez, Hialeah, FL (US)

(73) Assignee: Eugenio Perez, Hialeah, FL (US)

( * ) Notice: Subject to any disclaimer, the term of this patent is extended or adjusted under 35 U.S.C. 154(b) by 1145 days.

(21) Appl. No.: 11/926,889

(22) Filed: Oct. 29, 2007

(51) Int. Cl.
*A61H 15/00* (2006.01)
*A61H 7/00* (2006.01)
*A61H 19/00* (2006.01)

(52) U.S. Cl.
USPC .......................................... 601/138; 601/114

(58) Field of Classification Search
USPC ............... 601/17, 50, 55, 75, 86, 87, 88, 112, 601/114, 136, 154, 85, 138; 606/131, 133; 607/79, 85, 86; 4/606, 621, 622, 628; 15/28, 29
See application file for complete search history.

(56) References Cited

U.S. PATENT DOCUMENTS

| | | | |
|---|---|---|---|
| 3,612,052 A * | 10/1971 | Krummenacher | 604/23 |
| 3,733,634 A | 5/1973 | Globe | |
| 3,810,463 A * | 5/1974 | Krummenacher | 601/114 |
| D264,164 S | 5/1982 | Salibello et al. | |
| 5,891,063 A | 4/1999 | Vigil | |
| 6,139,553 A * | 10/2000 | Dotan | 606/131 |
| 6,374,446 B1 | 4/2002 | Gleason | |
| 6,523,546 B2 | 2/2003 | Jo et al. | |
| 6,568,000 B1 * | 5/2003 | Kaufman et al. | 4/622 |
| 6,575,171 B1 | 6/2003 | Jacquin | |
| 6,732,394 B1 | 5/2004 | Waterman | |
| 7,384,377 B2 * | 6/2008 | Berman | 482/11 |
| 2003/0126679 A1 * | 7/2003 | Leung et al. | 4/622 |
| 2005/0235411 A1 * | 10/2005 | Lev et al. | 4/622 |

* cited by examiner

*Primary Examiner* — Kristen Matter

(57) ABSTRACT

A skin exfoliation apparatus includes a housing and a receiving member that has base wall and a perimeter wall. The perimeter wall has an upper edge defining an opening into the receiving member. The receiving member is mounted to the housing. A motor is mounted within the housing. A drive shaft is mechanically coupled to the motor and extends upwardly through the base wall. The drive shaft is rotated when the motor is turned on. A plate has a top side and a bottom side. The bottom side is attached to the drive shaft. An abrasive surface is attached to the top side of the plate. The plate is rotated when the drive shaft is rotated by the motor. A body part is positioned on the abrasive surface to cause exfoliation of the skin on the body part.

13 Claims, 4 Drawing Sheets

SKIN EXFOLIATION APPARATUS

BACKGROUND OF THE INVENTION

Field of the Invention

The present invention relates to skin exfoliation devices and more particularly pertains to a new skin exfoliation device for exfoliating skin from a body part positioned in the device, such as an elbow.

SUMMARY OF THE INVENTION

The present invention meets the needs presented above by generally comprising a housing that has a top wall, a bottom wall and a peripheral wall attached to and extending between the top and bottom walls. A receiving member has base wall and a perimeter wall that is attached to and extends upwardly from the base wall. The perimeter wall has an upper edge defining an opening into the receiving member. The receiving member is mounted to the housing. A motor is mounted within the housing. A drive shaft is mechanically coupled to the motor and extends upwardly through the base wall. The drive shaft is rotated when the motor is turned on. A plate has a top side and a bottom side. The bottom side is attached to the drive shaft. An abrasive surface is attached to the top side of the plate. The plate is rotated when the drive shaft is rotated by the motor. A body part is positioned on the abrasive surface to cause exfoliation of the skin on the body part.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
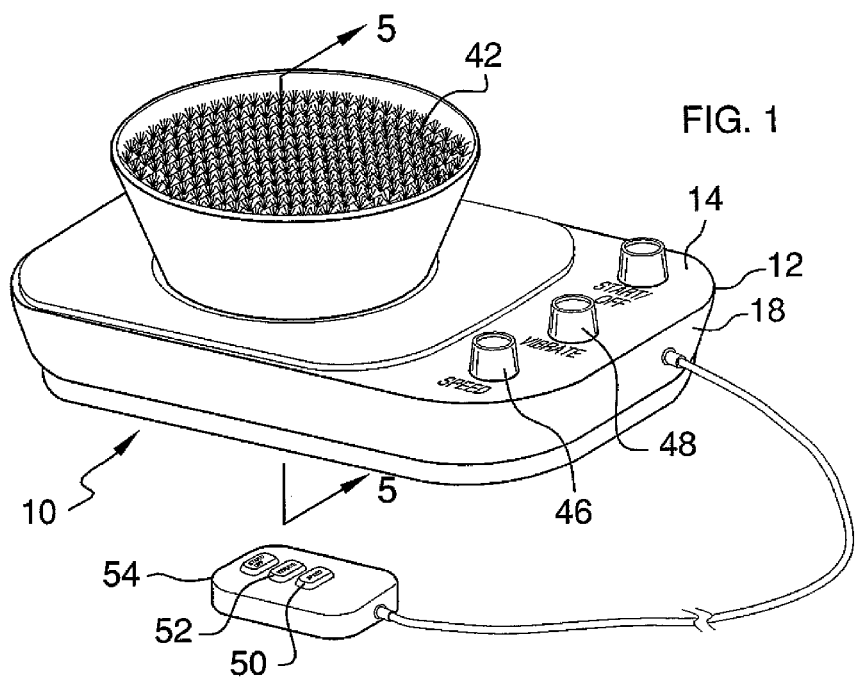
FIG. 1 is a perspective view of a skin exfoliation apparatus according to the present invention.
Figure 2:
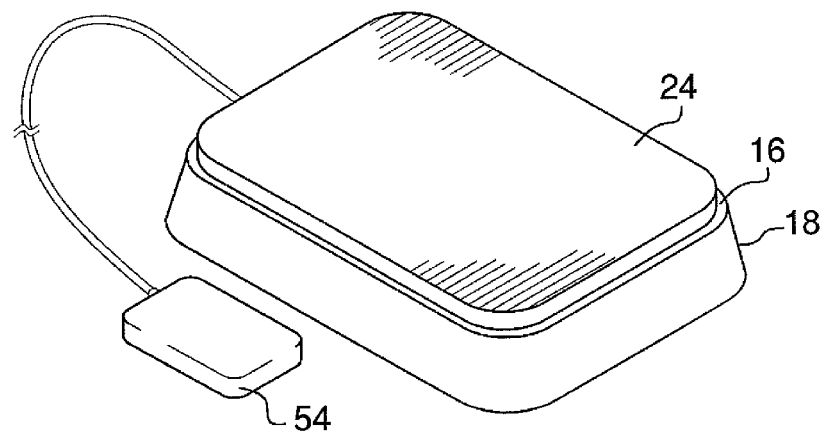
FIG. 2 is a bottom perspective view of the present invention.

With reference now to the drawings, and in particular to FIGS. 1 through 6 thereof, a new skin exfoliation device embodying the principles and concepts of the present invention and generally designated by the reference numeral 10 will be described.

As best illustrated in FIGS. 1 through 6, the skin exfoliation apparatus 10 generally comprises a housing 12 that has a top wall 14, a bottom wall 16 and a peripheral wall 18 attached to and extending between the top 14 and bottom 16 walls. A motor 20 is mounted within the housing 12. A power source 22 is electrically coupled to the motor 20 to supply electricity to the motor 20. The power source 22 may comprise a battery or an electrical plug plugged into an electrical outlet. A resiliently compressible pad 24 is attached to the bottom wall 16.

Figure 3:
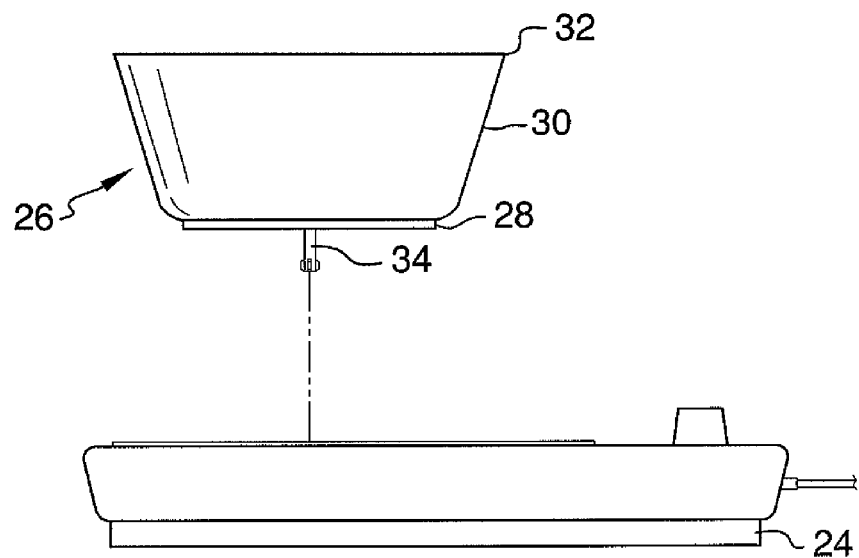
FIG. 3 is a side view of the present invention.
Figure 4:
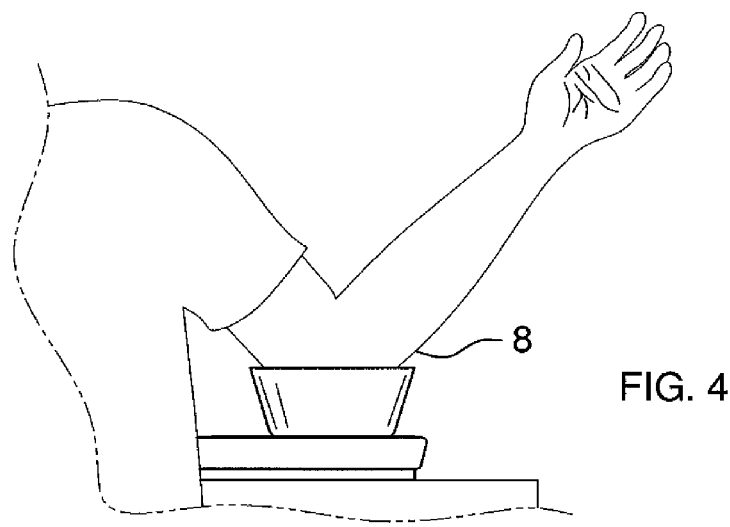
FIG. 4 is a side in-use view of the present invention.
Figure 5:
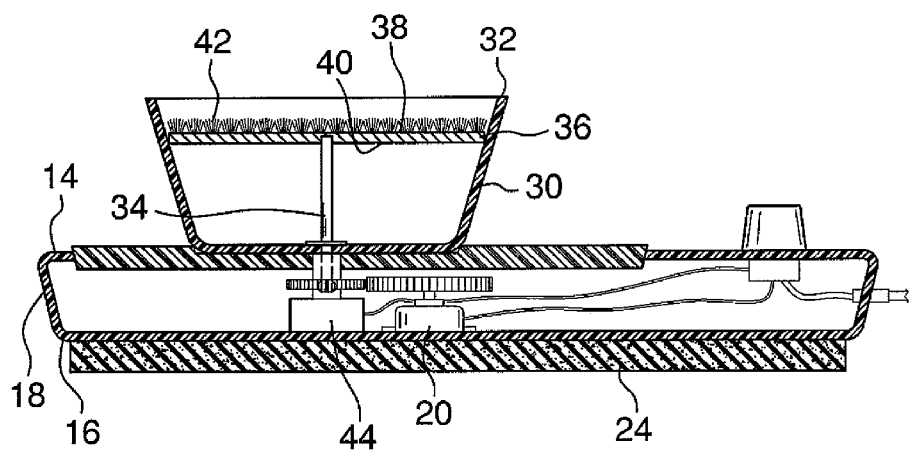
FIG. 5 is a cross-sectional view taken along line 5-5 of FIG. 1 of the present invention.
Figure 6:
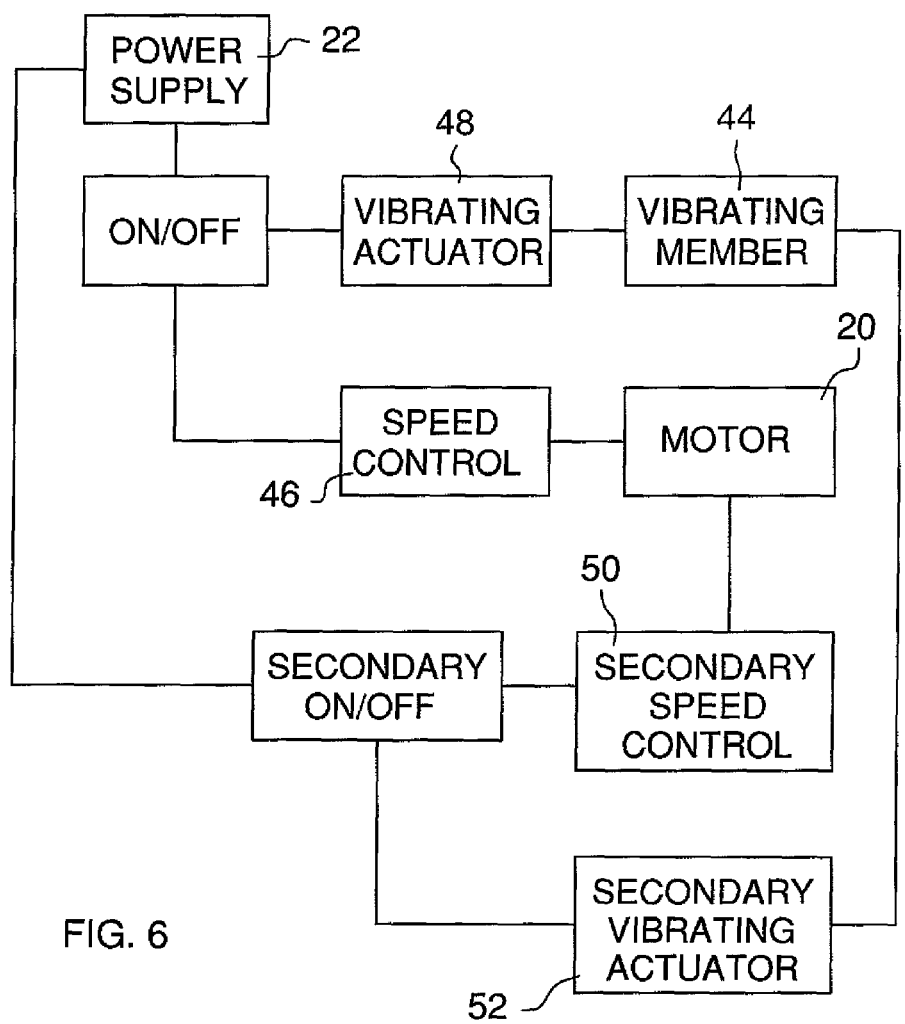
FIG. 6 is a schematic view of the present invention.

A receiving member 26 is provided for receiving a body part 8. The receiving member 26 has base wall 28 and a perimeter wall 30 that is attached to and extends upwardly from the base wall 28. The perimeter wall 30 has an upper edge 32 defining an opening into the receiving member 26. The receiving member 26 is mounted to the housing 12. The receiving member 26 may be detachably mounted to the housing 12 as shown in FIG. 3.

A drive shaft 34 is mechanically coupled to the motor 20 and extends upwardly through the base wall 28. The drive shaft 34 is rotated when the motor 20 is turned on. A plate 36 has a top side 38 and a bottom side 40. The bottom side 40 is attached to the drive shaft 34. An abrasive surface 42 is attached to the top side 38 of the plate 36. The abrasive surface 42 includes a plurality of bristles extending upwardly from the top side 38 of plate 36. The plate 36 is rotated when the drive shaft 34 is rotated by the motor 20. The plate 36 may be detached from the receiving member 26 to allow for the usage of different plates 36 having different types of abrasive surfaces 42.

A vibration member 44 is mechanically coupled to the drive shaft 34 and vibrates the plate 36 when the vibration member 44 is turned on. The vibrating motion assists in the exfoliation process.

A speed actuator 46 is electrically coupled to the motor 20. The speed actuator 46 is actuated to select a drive speed of the motor 20. The speed actuator 46 is mounted on the housing 12 along with a vibration actuator 48 for turning the vibration member 44 on or off. A secondary speed actuator 50 and secondary vibration actuator 52 may be mounted on a remote actuator 54 either wirelessly or electrically in communication with the vibration member 44 and the motor 20.

In use, the body part 8 is positioned on the abrasive surface 42 to cause exfoliation of the skin on the body part 8. The rotation of the plate 36 and the vibration of the plate 36 removes dead skin and calluses from the body part 8.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An exfoliating assembly to exfoliate skin from a body part abutted with said assembly, said assembly including:
    a housing having a top wall, a bottom wall and a peripheral wall being attached to and extending between said top and bottom walls, an abutting edge of said bottom wall and said peripheral wall bounding a first area, said housing having a height being less than a length or width of said housing;

a receiving member for receiving a body part, said receiving member having a base wall and a perimeter wall being attached to and extending upwardly from said base wall, said perimeter wall having an upper edge defining an opening into said receiving member, said receiving member being mounted to said housing, said upper edge defining an upper plane of said receiving member, an interior space being defined within said receiving member and being bounded by said base wall, said perimeter wall and said upper plane;

a motor being mounted within said housing;

a drive shaft being mechanically coupled to said motor and extending upwardly through said base wall, said drive shaft being rotated when said motor is turned on;

a plate having a top side and a bottom side, said bottom side being attached to said drive shaft, an abrasive surface being attached to said top side of said plate, said plate being rotated when said drive shaft is rotated by said motor, said plate having an outer edge bonding a second area, said second area being smaller than said first area to facilitate retaining of said housing in an upright position having said top wall facing upwardly, said plate and said abrasive surface being positioned completely within said interior space, said top side being directed upwardly and said housing being retained in an upright position when said motor is turned on; and wherein the body part is positioned on said abrasive surface to cause exfoliation of the skin on the body part.

2. The assembly according to claim 1, wherein said abrasive surface includes a plurality of bristles extending upwardly from said top side of plate.

3. The assembly according to claim 1, further including a vibration member being mechanically coupled to said drive shaft and vibrating said plate when said vibration member is turned on.

4. The assembly according to claim 1, further including a speed actuator being electrically coupled to said motor, said speed actuator being actuated to select a drive speed of said motor.

5. The assembly according to claim 1, said receiving member being removable from said housing.

6. The assembly according to claim 1, said receiving member being removable from said housing, said receiving member being positioned above said top wall such that said drive shaft extends upwardly through said top wall and upwardly through said base wall.

7. An exfoliating assembly to exfoliate skin from a body part abutted with said assembly, said assembly including:

a housing having a top wall, a bottom wall and a peripheral wall being attached to and extending between said top and bottom walls, an abutting edge of said bottom wall and said peripheral wall bounding a first area, said housing having a height being less than a length or width of said housing;

a receiving member for receiving a body part, said receiving member having a base wall and a perimeter wall being attached to and extending upwardly from said base wall, said perimeter wall having an upper edge defining an opening into said receiving member, said receiving member being mounted to said housing, said upper edge defining an upper plane of said receiving member, an interior space being defined within said receiving member and being bounded by said base wall, said perimeter wall and said upper plane;

a motor being mounted within said housing, said top wall of said housing remaining in a horizontal orientation when said motor is turned on;

a drive shaft being mechanically coupled to said motor and extending upwardly through said base wall, said drive shaft being rotated when said motor is turned on;

a plate having a top side and a bottom side, said bottom side being attached to said drive shaft, an abrasive surface being attached to said top side of said plate, said abrasive surface including a plurality of bristles extending upwardly from said top side of plate, said plate being rotated when said drive shaft is rotated by said motor, said plate having an outer edge bonding a second area, said second area being smaller than said first area to facilitate retaining of said housing in an upright position having said top wall facing upwardly, said plate and said abrasive surface being positioned completely within said interior space, said top side being directed upwardly and said housing being retained in an upright position when said motor is turned on;

a vibration member being mechanically coupled to said drive shaft and vibrating said plate when said vibration member is turned on;

a speed actuator being electrically coupled to said motor, said speed actuator being actuated to select a drive speed of said motor; and wherein the body part is positioned on said bristles to cause exfoliation of the skin on the body part.

8. The assembly according to claim 7, said receiving member being removable from said housing.

9. An exfoliating assembly to exfoliate skin from a body part abutted with said assembly, said assembly including:

a housing having a top wall, a bottom wall and a peripheral wall being attached to and extending between said top and bottom walls, an abutting edge of said bottom wall and said peripheral wall bounding a first area, said housing having a height being less than a length or width of said housing;

a receiving member for receiving a body part, said receiving member having a base wall and a perimeter wall being attached to and extending upwardly from said base wall, said perimeter wall having an upper edge defining an opening into said receiving member, said receiving member being mounted to said housing and above said top wall, said upper edge defining an upper plane of said receiving member, an interior space being defined within said receiving member and being bounded by said base wall, said perimeter wall and said upper plane;

a motor being mounted within said housing between said top and bottom walls;

a drive shaft being mechanically coupled to said motor and extending upwardly through said top wall and said base wall, said drive shaft being rotated when said motor is turned on;

a plate having a top side and a bottom side, said bottom side being attached to said drive shaft such that said base wall is positioned between said plate and said top wall, an abrasive surface being attached to said top side of said plate, said plate being rotated when said drive shaft is rotated by said motor, said plate having an outer edge bonding a second area, said second area being smaller than said first area to facilitate retaining of said housing in an upright position having said top wall facing upwardly, said plate and said abrasive surface being positioned completely within said interior space, said top side being directed upwardly and said housing being retained in an upright position when said motor is turned on; and wherein the body part is positioned on said abrasive surface to cause exfoliation of the skin on the body part.

10. The assembly according to claim 9, wherein said abrasive surface includes a plurality of bristles extending upwardly from said top side of plate.

11. The assembly according to claim 9, further including a vibration member being mechanically coupled to said drive shaft and vibrating said plate when said vibration member is turned on.

12. The assembly according to claim 9, further including a speed actuator being electrically coupled to said motor, said speed actuator being actuated to select a drive speed of said motor.

13. The assembly according to claim 9, said receiving member being removable from said housing.

* * * * *